United States Patent [19]
Bredt et al.

[11] Patent Number: 5,641,638
[45] Date of Patent: Jun. 24, 1997

[54] **MONOCLONAL ANTIBODIES AGAINST *MYCOPLASMA PNEUMONIAE*, HYBRIDOMAS PRODUCING THESE, METHODS FOR THE PREPARATION THEREOF, AND THE USE THEREOF**

[75] Inventors: Wolfgang Bredt, Freiburg; Bernhard Gerstenecker, Albstadt; Enno Jacobs, Freiburg; Wilhelm Schuy, Obererbach, all of Germany

[73] Assignee: Behringwerke Aktiengesellschaft, Marburg, Germany

[21] Appl. No.: 367,769

[22] Filed: Jan. 3, 1995

Related U.S. Application Data

[63] Continuation of Ser. No. 173,940, Dec. 28, 1993, abandoned, which is a continuation of Ser. No. 961,327, Oct. 15, 1992, abandoned.

[30] Foreign Application Priority Data

Oct. 17, 1991 [DE] Germany .......................... 41 34 297.6

[51] Int. Cl.$^6$ .......................... G01N 33/53; C07K 16/00; C12P 21/08
[52] U.S. Cl. .................. 435/7.32; 435/7.92; 435/7.94; 435/70.21; 435/340; 435/975; 436/547; 436/548; 530/388.1; 530/388.2; 530/388.4
[58] Field of Search ............... 435/7.32, 7.92, 435/7.94, 240.27, 975, 70.21; 530/388.1, 388.4, 825, 388.2; 436/547, 548

[56] References Cited

U.S. PATENT DOCUMENTS

| | | | |
|---|---|---|---|
| 4,376,110 | 3/1983 | David et al. | 435/5 |
| 5,084,561 | 1/1992 | Bredt et al. | 530/417 |

FOREIGN PATENT DOCUMENTS

| | | |
|---|---|---|
| 0332021A2 | 9/1989 | European Pat. Off. |
| 0334278A2 | 9/1989 | European Pat. Off. |

OTHER PUBLICATIONS

Hirschberg et al, "ELISA for detection of *Mycoplasma pneumoniae* antigens using monoclonal antibodies", APMIS, 99(5): 475–481 (May 1991).

Hirschberg et al, "Demonstration of Membrane Association and Surface Location of *Mycoplasma pneumoniae* Antigens Using Monoclonal Antibodies", J. Gen Microbiol., 135:613–621 (1989).

Gerstenecker et al, "Topological mapping of the P1-adhesion of *Mycoplasma pneumoniae* with adherence-inhibiting monoclonal antibodies", J. Gen. Microbiol., 136: 471–476 (1990).

Harlow et al. Antibodies, A Laboratory Manual, pp. 141–150, 231–239 Cold Spring Harbor Laboratory (1988).

Nachweis Von Spezifischen Antikörpern Und Antigenen Bei Patienten Mit *Mycoplasma Pneumoniae*–Infektionen, E. Jacobs et al., Diagnostik Von Infektionskrankheiten, 1:84–105 (1987).

Laboratory Diagnosis of *Mycoplasma Pneumoniae* Infection, T. W. Kok et al., Epidem. Inf. 101:669–684 (1988).

Tissue Cultures and Mycoplasmas, L. Hayflick, Texas Reports on Biology and Medicine 23:s 285–303 (1965).

*Primary Examiner*—Marianne P. Allen
*Assistant Examiner*—Patricia A. Duffy
*Attorney, Agent, or Firm*—Finnegan, Henderson, Farabow, Garrett & Dunner, L.L.P.

[57] ABSTRACT

The invention relates to monoclonal antibodies and fragments thereof which are specific for *Mycoplasma pneumoniae* P2 protein and have a cross-reactivity of 1% or less with five other species of the genus Mycoplasma and other pathogen species of the concomitant flora, and to methods for the preparation of the monoclonal antibodies according to the invention. The invention furthermore relates to hybridomas which produce the antibodies according to the invention, and to methods for the preparation thereof. Finally, the invention relates to the use of the monoclonal antibodies according to the invention for detecting *Mycoplasma pneumoniae* in a sample.

21 Claims, 1 Drawing Sheet

MONOCLONAL ANTIBODIES AGAINST *MYCOPLASMA PNEUMONIAE*, HYBRIDOMAS PRODUCING THESE, METHODS FOR THE PREPARATION THEREOF, AND THE USE THEREOF

This application is a continuation, of application Ser. No. 08/173,940 filed Dec. 28, 1993, now abandoned; which is a continuation of Ser. No. 07/961,327 filed Oct. 15, 1992, abandoned.

The invention relates to monoclonal antibodies and fragments thereof which are specific for *Mycoplasma pneumoniae* and have a cross-reactivity of 1% or less with other species of the genus Mycoplasma or other pathogen species of the concomitant flora, and to methods for the preparation of the monoclonal antibodies according to the invention. The invention furthermore relates to hybridomas which produce the antibodies according to the invention, and to methods for the preparation thereof. Finally, the invention relates to the use of the monoclonal antibodies according to the invention for detecting *Mycoplasma pneumoniae* in a sample.

*Mycoplasma pneumoniae* (*M. pneumoniae*) causes diseases of the upper and of the lower respiratory tract. Since *M. pneumoniae* is, in contrast to viruses, sensitive to antibiotics, rapid diagnosis has considerable therapeutic consequences. However, reliable differentiation of a *M. pneumoniae* infection from viral or bacterial infections with similar signs and symptoms has not hitherto been possible. The laboratory diagnostic methods for determining *M. pneumoniae* have likewise been unsatisfactory to date. Pathogen detection by cultivation has only confirmatory value because of the very long growth on exacting media (1 to 2 weeks). In most cases, at present the diagnosis is made by serological methods. The most commonly used test, the complement fixation test (CFT) uses a glycolipid extract from *M. pneumoniae* as antigen. However, antibodies against these glycolipids show cross-reactions both with bacteria (*Streptococcus MG intermedicus*) and with plant lipids or components of human cells and therefore give false-positive reactions.

False-positive CFT reactions of this type have been described in particular with diseases associated with cytolysis, for example pancreatitis, meningitis and carditis. Other available test methods are unsuitable for the routine detection of *M. pneumoniae* because they either are too time-consuming (for example immunofluorescence), can be used only in special laboratories (adherence inhibition test) or have a specificity as low as that of the CFT (ELISA with *M. pneumoniae* total extract).

Production of monoclonal antibodies against various proteins of *M. pneumoniae* has been described in several publications.

Monoclonal antibodies against the P1 protein (adhesin or 168 kd protein), with which it was possible to inhibit the binding of *M. pneumoniae* to erythrocytes, have been established (B. Gerstenecker and E. Jacobs, *Journal of General Microbiology* 136 (1990), 471).

A publication by E. Jacobs et al. (Diagnostik yon Infektionskrankheiten, Publisher: Projektträgerschaft Forschung im Dienste der Gesundheit in der Deutschen Forschungs- und Versuchsanstalt für Luft- und Raumfahrt e.V., Volume 1, (1987), 84) describes 2 monoclonal antibodies against adhesin. Both (moAK 14 C11, moAK 11G7) react with *M. pneumoniae* only in dot-blot methods but not in other immunometric methods. Furthermore, moAK 14 C11 shows cross-reactions with *M. salivarium* and *M. genitalium*, and moAK 11G7 shows cross-reactions with, for example, *Branhamella catarrhalis* (compare Table I).

Although well-established methods are available for the preparation of monoclonal antibodies, there are often still considerable difficulties in the production and selection of hybridoma cell lines which exclusively have particular advantageous properties.

Thus, the studies cited above show monoclonal antibodies which cross-react either with one or more Mycoplasma species or with other pathogen species in the concomitant flora such as, for example, *H. influenzae, N. meningitidis, S. pneumoniae* or *P. aeruginosa* in the biological samples to be investigated, where cross-reactivity was not ruled out or was tested only under certain test conditions.

The present invention was therefore based on the technical problem of preparing a monospecific antibody which reacts with *Mycoplasma pneumoniae* but shows no, or essentially no, cross-reactivity with other Mycoplasma species and the abovementioned other pathogen species of the concomitant flora. The solution of this technical problem is achieved by the embodiments defined in the claims.

The invention thus relates to an antibody and fragments thereof which is (are) specific for *M. pneumoniae* and shows (show) a cross-reactivity of 1% or less with other species of the genus Mycoplasma.

The term "fragments" designates the immunoreactive antibody fragments which are known per se to the person skilled in the art. Among these fragments, the F(ab')$_2$ fragments are preferred.

In a preferred embodiment, the monoclonal antibody according to the invention and the fragments thereof shows (show) a cross-reactivity of 1% or less with other pathogen species of the concomitant flora. The term "concomitant flora" means one or more pathogenic or apathogenic microorganisms which may occur at the same time and at the same site in the body. The monoclonal antibody according to the invention exhibits these advantageous specificity properties for example in a semimonoclonal solid-phase sandwich assay. A semimonoclonal solid-phase sandwich assay means a, for example, polyclonal trapping antibody which is bound to a solid phase and which binds the antigen such as, for example, a protein of *Mycoplasma pneumoniae*, and a, for example, monoclonal detecting antibody which detects the bound antigen by a subsequent indicator reaction. Examples of semimonoclonal solid-phase sandwich assays of this type are the antigen ELISA (capture ELISA) and the PI ELISA. The monoclonal antibody according to the invention can be used for detecting *M. pneumoniae* furthermore in various methods known per se to the person skilled in the art, for example immunoblot, cell ELISA, precipitation, indirect EIA.

In a particularly preferred embodiment, the monoclonal antibody according to the invention and the fragments thereof is (are) specific for the P1 protein of *Mycoplasma pneumoniae*. The P1 protein is also known to the person skilled in the art as adhesin or 168 kd protein.

In another preferred embodiment, the heavy chain of the monoclonal antibody according to the invention or of the fragments thereof belongs to the γ1 subclass and the light chain belongs to the κ class.

In another preferred embodiment, the heavy chain belongs to the γ3 subclass and the light chain to the κ class.

The immunoglobulin classes and subclasses are determined by methods known per se to the person skilled in the art. The antibodies according to the invention can furthermore be characterized by methods known per se, for example with respect to their electrophoretic focusing pattern or their affinity constant.

The invention further relates to a hybridoma which produces one of the monoclonal antibodies according to the invention.

In a preferred embodiment of the hybridoma according to the invention, the spleen cell used for the fusion is derived from a BALB/c mouse.

In another preferred embodiment of the hybridoma according to the invention, the myeloma cell used for the fusion is X63/Ag8.653.

The invention further relates to the hybridoma line M57. The invention further relates to the hybridoma line M74. The invention further relates to the hybridoma line P1.25.

The invention further relates to the hybridoma line P1.27.

The invention further relates to the hybridoma line M75.

These hybridomas derive from two different fusions for which the myeloma cells of the line X63/Ag8.653 and spleen cells from BALB/c mice which had been immunized either with M. pn cells (fusion M) or purified P1 protein (fusion P1) had been used. All 5 hybridoma lines have secreted stable antibodies of one specificity in cell culture for 1 year. The antibodies secreted by all five hybridomas are specific for the P1 protein; none of these antibodies shows a significant cross-reaction with other Mycoplasma species such as M. genitalium, M. hominis, M. fermentans, M. salivarium or M. orale. These Mycoplasma species may occur with M. pneumoniae in the concomitant flora and impede unambiguous diagnosis of M. pneumoniae in the state of the art.

The hybridomas were deposited on Apr. 11, 1991 and on May 24, 1991, at the PHLS Centre for Applied Microbiology & Research, Porton Down, Salisbury, Wilts. SP4 0JG, England under the ECACC accession numbers 91041010 (M57), 91041011 (M74), 91041012 (P1.25), 91041013 (P1.27) and 91052310 (M75).

The invention further relates to a kit for detecting *Mycoplasma pneumoniae* in a sample, which kit contains at least one monoclonal antibody according to the invention. The kit according to the invention is preferably based on immunochemical heterogeneous or homogeneous determination methods known per se to the person skilled in the art, with particle-enhanced nephelometry or turbidimetry being preferred among the homogeneous methods.

In a particularly preferred embodiment of the kit according to the invention, *M. pneumoniae* is detected by a solid-phase immunometric system. Solid-phase immunometric systems are preferably employed in the heterogeneous immunoassays. A preferred example of a heterogeneous immunoassay is the solid-phase-bound sandwich assay in which the solid phase is preferably a polystyrene tube, a microtiter plate, a latex particle, a magnetizable particle or a sheet-like solid phase.

The invention further relates to a method for the preparation of a hybridoma according to the invention, wherein (a) a mouse is immunized with *Mycoplasma pneumoniae* cells or the P1 protein of *Mycoplasma pneumoniae*, (b) spleen cells from the immunized mouse are fused with suitable myeloma cells, and (c) the hybridomas obtained in step (b) are selected for secretion of antibodies which are specific for *M. pneumoniae* and show a cross-reactivity of 1% or less with other species of the genus Mycoplasma.

The invention further relates to a method for the preparation of a hybridoma according to the invention, wherein (a) a mouse is immunized with *Mycoplasma pneumoniae* cells or the P1 protein of *Mycoplasma pneumoniae*, (b) spleen cells from the immunized mouse are fused with suitable myeloma cells, and (c) the hybridomas obtained in step (b) are selected for secretion of antibodies which are specific for *M. pneu-*

*moniae* and show a cross-reactivity of 1% or less with other species of the genus Mycoplasma; and (d) the hybridomas obtained in step (c) are selected for secretion of antibodies which show a cross-reactivity of 1% or less with other pathogen species of the concomitant flora.

The hybridomas according to the invention are prepared by immunizing mice with a suitable immunogen (*M. pneumoniae* cells or P1 protein) by methods known per se (compare, for example Harlow and Lane, "Antibodies", Cold Spring Harbor Laboratory, Cold Spring Harbor, 1988).

In a preferred embodiment, the mice used for the immunization are BALB/c mice. The immunizations are carried out with an interval of at least one week. The mice are preferably immunized at least twice, with the final immunization preferably being intravenous and/or intraperitoneal. The antibody titer is checked after each immunization. To do this, a blood sample is taken from the mice 3 to 5 days after injection of the immunogen, and serum is obtained from this by methods known per se and tested for the titer of *M. pneumoniae*- or P1-specific antibodies. If the titer is sufficiently high, the mice are sacrificed, the spleens are removed and the individual spleen cells are detached from the tissue under sterile conditions. The spleen cells are washed one or more times and then fused with cells of a mouse myeloma line.

In a preferred embodiment, the myeloma line used for the fusion is X63/Ag 8.653. A ratio of spleen cells to myeloma cells of 2:1 to 10:1 is preferably used for the fusion. Polyethylene glycol is preferably used as fusion promoter. However, other fusion promoters are also available, such as, for example, the sendai virus.

After the fusion, the cells are inoculated onto microtiter plates, preferably on plates with 96 wells. Macrophages or thymocytes from syngenic or congenic mice, which secrete factors promoting the growth of hybridomas, for example interleukin 6, have been added to the microtiter plates preferably on the preceding day.

The growth medium used is a selective medium, preferably HAT medium. The spleen cells have only limited viability in cell culture and die after a few cell divisions. The myeloma cell line chosen as fusion partner has a defect in an enzyme which is involved in nucleotide synthesis (for example hypoxanthine-guanine phosphoribosyltransferase) and is thus unable to live in HAT medium. Only hybridomas which have received the intact enzymatic apparatus from the spleen cell and the capability of unlimited growth in cell culture from the myeloma cell survive in the selection medium.

The wells of the microtiter plates are examined for the growth of hybridomas after 1 to 2 weeks. The growth medium in hybridoma-positive wells is subsequently tested for the presence of antibodies with the required properties. The test system in this case is usually aimed at the properties of the immunogen or antigen.

Hybridomas which secrete antibodies with the required properties are subcloned at least once by the limiting dilution method in order to ensure their clonality. The cells are normally diluted until, viewed statistically, 0.5 to 3 cells grow per well. In addition, the subcloning method has proven advantageous in the preparation of hybridomas with stable properties. The methods for preparing hybridomas are described in detail for example in Harlow and Lane, loc. cit., Melchers, Potter and Warner, Editors, "Lymphocyte Hybridomas", Springer-Verlag, Berlin, 1979 and in J. H. Peters and H. Baumgarten, Monoclonale Antikörper, Herstellung und Charakterisierung (Monoclonal Antibodies, Preparation and Characterization), Springer-Verlag, Berlin 1990.

The invention further relates to the preparation of a monoclonal antibody according to the invention, wherein a hybridoma according to the invention (a) is cultured in vitro; and (b) the monoclonal antibody is obtained from the culture medium.

The invention further relates to the preparation of a monoclonal antibody according to the invention, wherein a hybridoma according to the invention (a) is cultured in vivo in the peritoneal cavity of a syngenic or congenic mouse; and (b) the monoclonal antibody is obtained from the ascites fluid.

Larger amounts of the monoclonal antibodies according to the invention can be obtained by methods known per se to the person skilled in the art by in vitro cell culture of the hybridomas according to the invention and subsequently purifying and obtaining from the supernatant or by in vivo cultivation of the hybridomas in the peritoneal cavity of congenic or syngenic mice and subsequent purification of the antibodies from the ascites fluid (compare Harlow and Lane, loc. cit.).

The invention further relates to the use of a monoclonal antibody according to the invention for detecting *Mycoplasma pneumoniae* in a sample.

The monoclonal antibodies according to the invention can be used within the scope of a diagnostic method, in which case at least one of the antibodies is employed as specific binding partner for the *M. pneumoniae* antigen. The second specific binding partner can be another antibody or an antibody fragment, a lectin or a receptor. The monoclonal antibodies according to the invention are preferably used in a diagnostic method, preferably in a one-step assay, in which the second specific binding partner is also a monoclonal antibody according to the invention, which recognizes a different epitope than the first specific binding partner.

For detection and quantification in this case it is possible for one of the specific binding partners to carry a detectable label. These labels are known per se to the person skilled in the art and can be, for example, a chromophore, a luminophore, a fluorophore, an enzyme, a radioactive isotope or a colored or uncolored particle.

Preferred methods for preparing antibody-coated solid phases are those which bind the unlabeled specific binding partners by methods known per se to the person skilled in the art directly or indirectly, for example via another antibody or a biotin-avidin bridge which is coupled to a solid phase.

Figure 1:
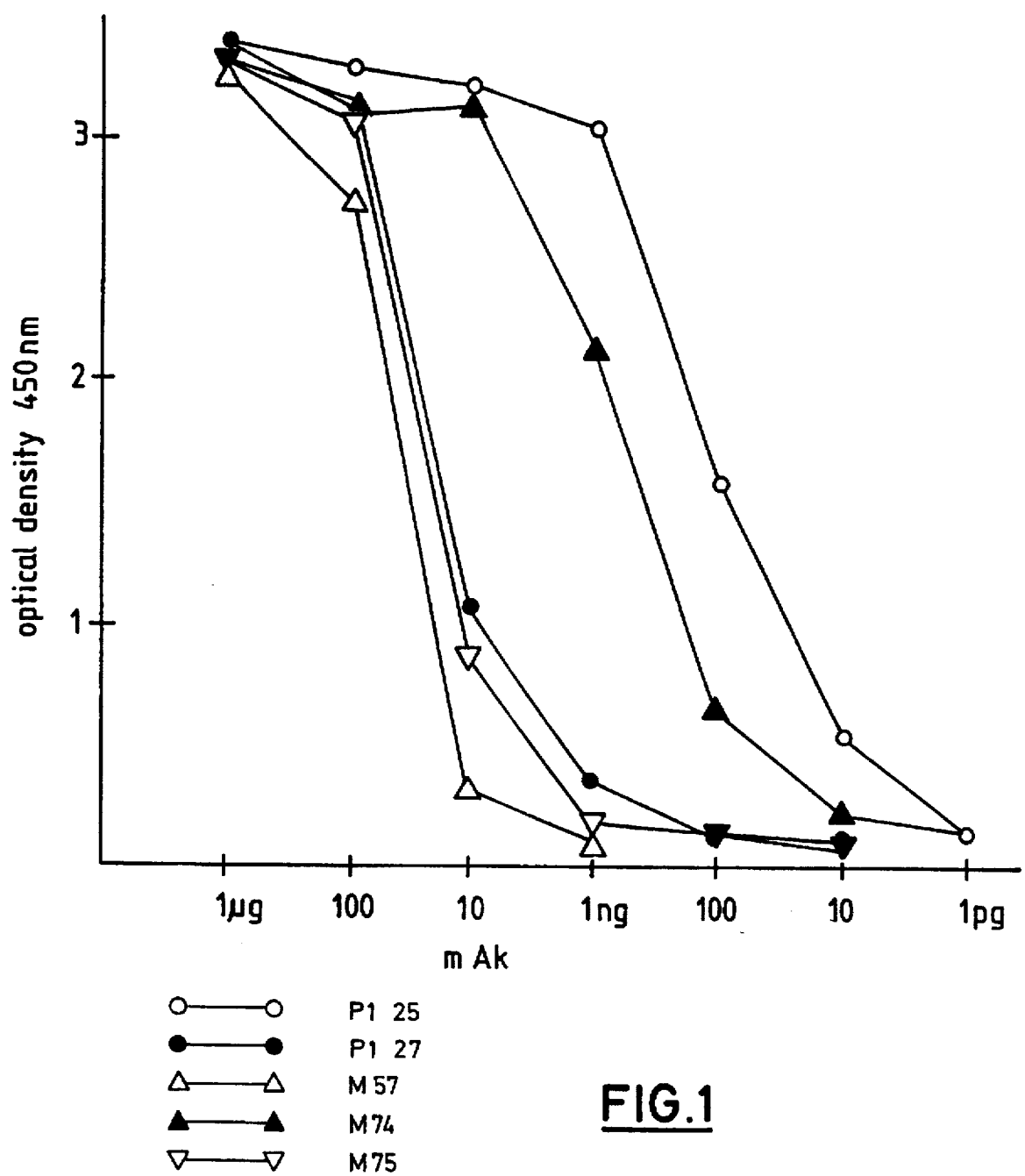
FIG. 1 shows the avidity for *Mycoplasma pneumoniae* of the monoclonal antibodies secreted by the hybridomas M57, M74, P1.25, P1.27 and M75 on the basis of standard dilution plots, compared Example 6.

The examples illustrate the invention.

EXAMPLE 1

Semimonoclonal Double-Sandwich Test

A. Preparation of Trapping Antibodies

Rabbits (cross of German Giant and Large Chinchilla) were immunized with 0.5 mg of *M. pneumoniae* protein as described by T. W. Kok et al. in Epidem. Inf. 101 (1988), 669. The IgG fraction of the immune serum was purified by gel permeation chromatography. To do this, the serum was loaded onto a Sephacryl®S-300 superfine column (Pharmacia) equilibrated with 50 mM tris/HCl (pH 8.0), and the IgG fraction was eluted with 500 mM NaCl.

B. Coating of Microtiter Plates with Rabbit Antibodies

Microtiter plates with 96 wells supplied by NUNC (Roskilde, Denmark) were coated with purified rabbit anti-*M. pneumoniae* antibodies (compare A above) as described in European Patent Application 89103478.

C. Procedure for the Semimonoclonal Double-Sandwich Test (Capture Assay)

0.1 ml of cells of *M. pneumoniae* and other "non-*Mycoplasma pneumoniae* species" of the concomitant flora, solubilized with sample buffer STD (product No.: OUWO; Behringwerke AG, Marburg, FRG) (various dilutions from 1 µg to 0.4 ng in sample buffer STD) was incubated in a microtiter plate, which was coated as described under B, at 37° C. for 1 hour. This was followed by three washes with 0.3 ml of washing solution POD (product No.: OSEW, Behringwerke AG, Marburg, FRG). 0.1 ml per well of the microtiter plate of the monoclonal antibody to be tested (compare Table I), diluted in conjugate buffer microbiol. (product No.: OUWW, Behringwerke AG, Marburg, FRG) was incubated at 37° C. for 30 minutes. Three washes where then carried out as described above. The test system was subsequently incubated with 0.1 ml of an anti-mouse IgG/POD conjugate (product No.: NCIK03, Behringwerke AG, Marburg, FRG), diluted 1:8000 in conjugate buffer microbiol., at 37° C. for 60 minutes. Three washes were then carried out as described previously. For color development, 0.1 ml of TMB chromogen solution ready for use was pipetted into each well. The color development was stopped after incubation at room temperature for 30 minutes with stop solution POD.

Chromogen solution ready for use was made up from the reagents in the kit "Additional Reagents for Enzygnost®/TMB" (product No.: OUVP, Behringwerke AG, Marburg, FRG) and in accordance with the instructions contained therein. The abovementioned kit also contains stop solution POD. The color development was determined with a photometer for microtiter plates (Behring ELISA Processor II; Behringwerke AG, Marburg). The wavelength for measurement was 450 nm, and 650 nm was used as correction wavelength.

EXAMPLE 2

Procedure for a Homogeneous Polyclonal Capture ELISA

The binding of other Mycoplasma species (*M. genitalium, M. fermentans, M. hominis, M. salivarium, M. orale*) by the rabbit serum raised against *M. pneumoniae* was detected in a homogeneous polyclonal capture ELISA. In this assay the rabbit serum was used both as the trapping antibody bound to the solid phase and as secondary detector antibody. The binding of the detector antibody, which was conjugated with biotin by methods known in the state of the art, was detected by an avidin/POD conjugate known per se.

The procedure for the test is identical to that described in Example 1 for the semimonoclonal double-sandwich test, with the exception of the detection system.

EXAMPLE 3

Preparation of Monoclonal Anti-*Mycoplasma pneumoniae* Antibodies

A. Growth of *Mycoplasma pneumoniae*

*M. pneumoniae* strain FH was grown in Hayflick's modified Eagle's medium (L. Hayflick in Texas Reports on Biology and Medicine 23 (1965), 285). The cells were sedimented by centrifugation (1000×g, 10 minutes) and washed twice in sterile phosphate-buffered saline solution (PBS).

B. Preparation of P1 Protein

The purification of P1 protein from *M. pneumoniae* is described in European Patent Application 89105006.

C. Immunizations

Male BALB/c mice between 6 and 8 weeks of age were immunized intraperitoneally with about $10^8$ colony-forming units of freshly harvested and washed intact *M. pneumoniae* cells in PBS or with 500 µg of purified P1 protein emulsified in complete Freund's adjuvant (CFA). For the immunizations, the P1 protein was separated from excess detergent (SDS) before emulsion in CFA and after purification by chloroform-methanol extraction, and was subsequently resuspended in PBS by ultrasound treatment.

The immunizations were repeated 4 times at 10-day intervals. 4 days after the final immunization, the mice were sacrificed after determination of the antibody titer, and the spleens were removed for the preparation of hybridomas.

D. Fusion

After combining, the spleen cells were fused with cells of the myeloma line X63/Ag8.653. The fusion promoter used was polyethylene glycol (PEG) 1500 [50% (weight/volume) PEG 1500 in 75 mM HEPES, 5% (vol./vol.) DMSO] (dropwise addition of PEG (1 ml) over a period of 1 minute). The fusion mixture was subsequently diluted in serum-free medium and carefully washed. The cell sediment was resuspended in HAT selection medium and plated out at a density of $2\times10^5$ cells per ml in microtiter plates with 96 wells in the presence of peritoneal macrophages.

Selection in HAT medium took place for 7 to 10 days. Immediately after completion of the selection phase, the hybridomas were changed to HT medium.

E. Selection of Hybridomas which Secrete *M. pneumoniae*-specific Antibodies After completion of the selection method in HAT medium, 100 hybridomas from the P1 fusion and 472 hybridomas from the M fusion were examined by the method described in Example 1 for the secretion of *M. pneumoniae*-specific antibodies. A total of 37 hybridomas secreted antibodies which reacted with solubilized *M. pneumoniae* cells but not with the rabbit serum antibodies bound to the solid phase.

The antibodies secreted by these 37 hybridomas were examined in ELISA test systems by methods known per se for reactivity with immobilized P1 protein, with total cell extract disrupted by ultrasound, with partially fixed, undamaged *M. pneumoniae* cells and by radioimmunoprecipitation for binding of the P1 protein and other *M. pneumoniae* surface structures.

The antibodies were furthermore examined for cross-reactivity with other Mycoplasma species (*M. genitalium, M. fermentans, M. hominis, M. salivarium, M. orale*) by the method described in Examples 1 and 2. The cross-reactivity is defined in percentages in this case. These percentages were established by employing equal amounts (100 µg/ml; 0.1 ml) of the various Mycoplasma species in a test series. The binding of the antibodies to *M. pneumoniae* and the values obtained thereby for the color development are set equal to 100%. The values obtained for the other Mycoplasma species and thus the cross-reactivity are related to this 100%.

In contrast to the polyclonal rabbit anti-*M. pneumoniae* sera, no cross-reactivity with other Mycoplasma species was detectable for the five monoclonal antibodies secreted by the hybridomas according to the invention. The results are summarized in Table I.

F. Cloning under Limiting Conditions

The oligoclonal hybridoma cultures which did not cross-react with other Mycoplasma species were expanded in order to have sufficient numbers of cells available for cloning under limiting conditions.

To do this, the cultures were harvested in the exponential phase of growth, and the number of live cells was determined by staining with trypan blue, a method known per se to the person skilled in the art. The cell count was adjusted to one hybridoma cell per well in a microtiter plate with 96 wells, and the hybridomas were cultivated in the presence of peritoneal macrophages as feeder layer. After 14 days, the hybridoma cultures, which were now monoclonal as a result of the subcloning, were examined by the method described in Examples 1 and 2 for the continuous secretion of *M. pneumoniae*-specific antibodies and for the cross-reactivity thereof with other Mycoplasma species.

All the examined hybridomas secreted antibodies continuously over a period of 1 year.

The results of the specificity and cross-reactivity tests are presented in Table I.

G. Determination of the Immunoglobulin (Ig) Classes

The Ig classes and Ig subclasses were determined with a capture immunoassay. Ig class- and subclass-specific polyclonal antibodies were coupled to nitrocellulose sheets (trapping phase). The monoclonal antibodies which had been partially purified from ascites fluids and labeled with biotin were incubated with the trapping phase. Trapped antibodies were detected with streptavidin-peroxidase.

The monoclonal antibodies P1.25 and M74 belong to the IgG1 subclass, and P1.27, M57 and M75 belong to the IgG3 subclass; all the monoclonal antibodies have light chains of the $\chi$ type.

EXAMPLE 4

Production of Monoclonal Antibodies in vivo (Ascites Production)

The immune system of female BALB/c mice between 6 and 8 weeks of age was activated by intraperitoneal injection of 0.5 ml of incomplete Freund's adjuvant. 24 hours after this injection, the animals received intraperitoneal administration of a suspension of $10^6$ hybridoma cells from a clone. After development of the tumors for 2 to 6 weeks, the animals were sacrificed and the ascites fluid was removed by puncture. The capture ELISA (compare Example 1) was used to detect high antibody concentrations in the puncture fluids.

EXAMPLE 5

Specificity for *Mycoplasma pneumoniae* of the Monoclonal Antibodies Secreted by the Hybridomas M57, M74, P1.25, P1.27 and M75

The antibodies secreted by the clonal hybridomas M25, M51, M57, M74, P1.25, P1.27 and M75, as well as two polyclonal rabbit antisera raised against *M. pneumoniae* were examined by the methods described in Examples 1 and 2 and the antibody secreted by the clonal hybridoma 11G7 was examined in a dot-blot, a method known per se, for specificity for *M. pneumoniae* and a possible cross-reactivity with other Mycoplasma species. The result is presented in Table I. It is evident from this that M57, M74, P1.25, P1.27 and M75 are monospecific for epitopes of *M. pneumoniae*, while M25, M51, 11G7 and the two rabbit antisera cross-react with other "non-*Mycoplasma pneumoniae* species".

EXAMPLE 6

Avidity for *Mycoplasma pneumoniae* of the Monoclonal Antibodies Secreted by the Hybridomas M57, M74, P1.25, P1.27 and M75

FIG. 1 shows standard dilution plots for the monoclonal antibodies. The test was carried out as described in Example 1, with the amount of solubilized *Mycoplasma pneumoniae* cells being constant at 1 µg and the monoclonal antibodies being diluted in sample buffer microbiol. as shown in FIG. 1 for the tests.

7. The hybridoma P1.27 deposited as ECACC accession number 91041013.

8. The hybridoma M75 deposited as ECACC accession number 91052310.

9. A kit for detecting *Mycoplasma pneumoniae* in a sample, which contains at least one antibody as claimed in claim 1 and a detectable label.

10. The kit as claimed in claim 9, wherein said kit comprises a solid phase immunometric system to detect *Mycoplasma pneumoniae*.

11. A method for the detection and determination of *Mycoplasma pneumoniae* antigen P1 in a sample comprising the steps of a) immobilizing a first specific binding partner to a solid phase;

b) reacting the sample with the immobilized first specific binding partner and c) detecting any bound *Mycoplasma pneumoniae* antigen P1 by means of a second specific binding partner, wherein at least one binding partner is the antibody of claim 1.

TABLE I

Cross-reactivity of monoclonal antibodies and of the polyclonal trapping antibodies in the capture ELISA (antigen ELISA)

| | PERCENTAGE CROSS-REACTIVITY | | | | | | | | | |
|---|---|---|---|---|---|---|---|---|---|---|
| | monoclonal antibodies[1] | | | | | | | | polyclonal trapping antibodies[2] | |
| Pathogen | P1.25 | M74 | P1.27 | M57 | M75 | M25 | M51 | 11G7[3] | anti-Mpn | anti-P1 |
| M. pneumoniae | 100 | 100 | 100 | 100 | 100 | 100 | 100 | +++ | 100 | 100 |
| M. genitalium | <1 | <1 | <1 | <1 | <1 | 18.5 | 21.2 | – | 43.7 | 0 |
| M. hominis | <1 | <1 | <1 | <1 | <1 | 37 | 39.4 | – | 59.2 | 48 |
| M. fermentans | <1 | <1 | <1 | <1 | <1 | 11.1 | 16.6 | – | 69 | 3.7 |
| M. salivarium | <1 | <1 | <1 | <1 | <1 | 64.8 | 53 | – | 26.3 | 55.5 |
| M. orale | <1 | <1 | <1 | <1 | <1 | 7.4 | 10.6 | – | 52.5 | 25.9 |
| H. influenzae | <1 | <1 | <1 | <1 | <1 | <1 | <1 | + | <1 | <1 |
| B. catarrhalis | <1 | <1 | <1 | <1 | <1 | <1 | <1 | +/– | <1 | <1 |
| N. meningitidis | <1 | <1 | <1 | <1 | <1 | <1 | <1 | + | <1 | <1 |
| S. pneumoniae | <1 | <1 | <1 | <1 | <1 | <1 | <1 | – | <1 | <1 |
| P. aeruginosa | <1 | <1 | <1 | <1 | <1 | <1 | <1 | +/– | <1 | <1 |

[1]tested in the capture ELISA; polyclonal trapping antibody: anti-*M. pneumoniae* IgG
[2]tested in the homogeneous polyclonal capture ELISA; trapping antibody and detector antibody (biotin-labeled) were identical
[3]tested in the dot-blot system; mAb 11G7 did not react in the capture ELISA, irrespective of the specificity of the trapping antibody. Since a dot-blot method was used there was no measurement of the optical density. This means that no calculation of the percentages is possible.

We claim:

1. A monoclonal antibody or fragments thereof, which react specifically with P1 protein of *Mycoplasma pneumoniae* and show a cross-reactivity of 1% or less with five other species of the genus Mycoplasma.

2. A monoclonal antibody and fragments thereof as claimed in claim 1, which show a cross-reactivity of 1% or less with other pathogen species of the concomitant flora.

3. A hybridoma which produces an antibody or fragments thereof as claimed in claim 1.

4. A hybridoma as claimed in claim 3, wherein the hybridoma is derived from a fusion using a spleen cell from a BALB/c mouse.

5. A hybridoma as claimed in claim 3, wherein the hybridoma is derived from a fusion using a myeloma cell that is X63/Ag8.653.

6. The hybridoma M57 deposited as ECACC accession number 91041010.

12. The monoclonal antibody of claim 1, wherein a heavy chain of said monoclonal antibody belongs to the γ3 subclass and a light chain of said monoclonal antibody belongs to the κ class.

13. A monoclonal antibody and fragments thereof, which react specifically with P1 protein of *Mycoplasma pneumoniae* and show a cross-reactivity of 1% or less with the species *M. genitalium*, *M. hominis*, *M. fermentens*, *M. salivarium*, and *M. orale* of the species of the genus Mycoplasma.

14. The monoclonal antibody of claim 13, wherein a heavy chain of said monoclonal antibody belongs to the γ3 subclass and a light chain of said monoclonal antibody belongs to the κ class.

15. A monoclonal antibody and fragments thereof as claimed in claim 13, which show a cross-reactivity of 1% or less with other pathogen species of the concomitant flora.

16. A hybridoma which produces an antibody or fragments thereof as claimed in claim 13.

17. A hybridoma as claimed in claim 16, wherein the hybridoma is derived from a fusion using a spleen cell from a BALB/c mouse.

18. A hybridoma as claimed in claim 16, wherein the hybridoma is derived from a fusion using a myeloma cell that is x63/Ag8.653.

19. A kit for detecting *Mycoplasma pneumoniae* in a sample, which contains at least one antibody as claimed in claim 13 and a detectable label.

20. A method for the detection and determination of *Mycoplasma pneumoniae* antigen P1 in a sample comprising the steps of a) immobilizing a first specific binding partner to a solid phase;

b) reacting the sample with the immobilized first specific binding partner and c) detecting any bound *Mycoplasma pneumoniae* antigen P1 by means of second specific binding partner, wherein at least one binding partner is the antibody claim 13.

21. The kit as claimed in claim 19 further comprising means for performing a solid phase immunoassay.

* * * * *

UNITED STATES PATENT AND TRADEMARK OFFICE
CERTIFICATE OF CORRECTION

PATENT NO. : 5,641,638
DATED : June 24, 1997
INVENTOR(S) : Wolfgang BREDT et al.

It is certified that error appears in the above-indentified patent and that said Letters Patent is hereby corrected as shown below:

On the Title page, item [57], line 3 of the Abstract, delete "P2 protein" and insert --P1 protein--.

Claim 15, column 10, line 63, "monodonal" should read --monoclonal--.

Signed and Sealed this

Seventh Day of October, 1997

*Attest:*

BRUCE LEHMAN

*Attesting Officer*      *Commissioner of Patents and Trademarks*